United States Patent
Schmidt et al.

(10) Patent No.: US 8,974,832 B1
(45) Date of Patent: Mar. 10, 2015

(54) NUTRITIONAL PRODUCT COMPOSITION FOR INCREASING HUMAN GROWTH HORMONE AND NITRIC OXIDE PRODUCTION

(71) Applicant: Lifewave, Inc., San Diego, CA (US)

(72) Inventors: David Schmidt, San Diego, CA (US); Steve Haltiwanger, San Diego, CA (US)

(73) Assignee: Lifewave, Inc., San Diego, CA (US)

( * ) Notice: Subject to any disclaimer, the term of this patent is extended or adjusted under 35 U.S.C. 154(b) by 0 days.

(21) Appl. No.: 14/101,506

(22) Filed: Dec. 10, 2013

(51) Int. Cl.
*A61K 35/20* (2006.01)
*A61K 36/81* (2006.01)
*A61K 31/198* (2006.01)
*A61K 33/00* (2006.01)

(52) U.S. Cl.
CPC ............... *A61K 36/81* (2013.01); *A61K 31/198* (2013.01); *A61K 33/00* (2013.01); *A61K 35/20* (2013.01)
USPC ............................ 424/535; 424/724; 424/777

(58) Field of Classification Search
None
See application file for complete search history.

(56) References Cited

FOREIGN PATENT DOCUMENTS

WO      WO 2012/128982 A2 * 9/2012

* cited by examiner

*Primary Examiner* — Susan Hoffman
(74) *Attorney, Agent, or Firm* — ARC IP Law, PC; Josph J. Mayo

(57) ABSTRACT

A nutritional product composition for increasing human growth hormone and nitric oxide production, to increase lean muscle mass, decrease body fat, and improve cardiovascular function and immune function. The nutritional product composition includes a synergistic blend of nutrients and a silica gel that increases the rate of metabolism of cells to increase the rate of absorption of the nutrients and elevate the production of the human growth hormone and elevate nitric oxide production. The synergistic blend of nutrients includes colostrum, L-arginine, potassium citrate and goji berry extract. The silica gel increases an absorption rate of the synergistic blend.

10 Claims, No Drawings

NUTRITIONAL PRODUCT COMPOSITION FOR INCREASING HUMAN GROWTH HORMONE AND NITRIC OXIDE PRODUCTION

BACKGROUND OF THE INVENTION

1. Field of the Invention

One or more embodiments of the invention are related to the field of nutritional product compositions and methods of producing nutritional product compositions. Specifically, embodiments relate to nutritional product compositions for the mind, the heart, energy levels, the growth hormone and nitric oxide levels to improve health and wellness. Embodiments of the invention provide compositions that include a synergistic blend of a plurality of nutrients and a silica gel that increases an absorption rate of one or more nutrients in a user's body.

2. Description of the Related Art

Generally, nutrient deficiencies and toxicity in brain chemistry affect a user's mental awareness, behavior, memory, concentration and focus. Biochemical acetylcholine, associated with alpha brain waves produced by a user's brain neurons, is known to control brain speed. Acetylcholine, typically, allows information to easily travel between the cells. As such, low levels of acetylcholine may lead to an array of symptoms and diseases such as learning disorders, memory disturbances, attention deficiencies, and impaired thinking. Typically, nutritional supplements may re-establish the levels of acetylcholine that may be obtained from choline, for example. Generally, choline may be found in an array of foods such as eggs, meats, fish, vegetables, fruits and milk.

Known systems, for example, such as pills and juices for improving acetylcholine levels lack a nutrient delivery system that allows users to immediately obtain results. Typically, acetylcholine is difficult to elevate and requires large doses of the B vitamin choline supplied in mega doses. For example, the B vitamin choline may be in the form of choline chloride or choline bitartrate that is typically provided in 3 grams to 6 grams per day. Using typical methods of dosing between 1 gram to 2 grams or more per day of choline requires a duration of several weeks in order for a user to experience any benefits. As such, there is a need for a composition and method of making such a composition that rapidly elevates acetylcholine levels and does not depend on mega dosing or depend on a synthetic drug.

Typically, high blood pressure poses a risk of a user experiencing a stroke, and while medications may be used to lower blood pressure, such medications are associated with several side effects. Traditionally, for example, over 50% of the population has a magnesium deficiency. Using conventional oral supplements may take up to nine months in order to elevate serum magnesium levels. As such, there is a need for a composition and method of making such a composition that rapidly elevates magnesium levels with minimal to no side effects.

Generally, caffeine is considered to be the largest selling energy stimulant, wherein a majority of the population relies on coffee, tea and/or energy drinks for an increase in energy. Using typical solutions for increasing energy, however, such as caffeine or other stimulants, poses a problem of the user "crashing" after a time has lapsed. For example, caffeine and other stimulants may provide a user with a temporary boost of energy, however a rebound effect occurs, and a few hours after consumption the user is once again low on energy levels. Furthermore, for example, using typical systems may be harmful as some users are sensitive to caffeine resulting in an elevated blood pressure. In addition, typical energy drinks generally may include caffeine, sugar, sodium, artificial flavors, artificial colors, artificial preservatives, guarana and sodium benzoate. Such ingredients, for example, pose a variety of side effects that are harmful to the user. As such, there is a need for a composition and method of making such a composition that rapidly elevates energy levels and does not depend on one or more stimulants.

Typically, the human growth hormone is often referred to as the fountain of youth hormone and is associated with increases in lean muscle mass and decreases in body fat. In addition, generally, nitric oxide is often associated with cardiovascular health, hair growth, male sexual performance and immune function. Generally, elevating one or both of the human growth hormone and nitric oxide levels may lead to significant improvements in health. Traditionally, elevating the human growth hormone is often done by injecting a synthetic hormone into the user. However, using typical methods are extremely expensive and may lead to an array of side effects, such as bone enlargement. In addition, generally, natural materials for elevating the human growth hormone may be available, however in order to produce sufficient results, large doses of such materials, such as 10 grams or higher, is required. Furthermore, typically, elevating nitric oxide levels has been performed using one or more drugs such as hair loss and regrowth treatments and erectile dysfunction and impotence treatments. However, such drugs pose an array of side effects, and although natural materials may elevate nitric oxide levels, considerable amounts of time are required to produce efficient and significant results. As such, there is a need for a composition and method of making such a composition that elevates the human growth hormone and nitric oxide levels without the use of typical drugs.

Typically, silica gels are used as desiccants, as stationary phases in chromatography, as cat litter and food additives. Generally, silica gel absorbs moisture, dries air in industrial air systems and controls humidity. As a food additive, for example, silica gel is generally used as an anticaking agent, a defoaming agent, a chill-proofing agent and a filter aid.

In summary, known system generally include nutrient delivery mechanisms such as pills and fluids that require a vast amount of time for a user to experience benefits and results. There are no known nutritional product compositions that also include ingredients to increase the rate of metabolism of cells to increase the rate of absorption of the nutrients in order to rapidly elevate acetylcholine levels, rapidly normalize blood pressure and increase magnesium levels, rapidly elevate energy levels without the use of stimulants, and rapidly elevate human growth hormone levels and nitric oxide levels. In addition, there are no known nutritional product compositions that perform such functions while generally providing benefits within minutes without requiring megadosing. For at least the limitations described above there is a need for nutritional product compositions and methods of producing such compositions.

BRIEF SUMMARY OF THE INVENTION

One or more embodiments described in the specification are related to nutritional product compositions for the mind, the heart, increasing energy levels using intracellular adenosine triphosphate (ATP) production, and increasing human growth hormone and nitric oxide production. Furthermore embodiments described in the specification are related to methods of producing the nutritional product compositions.

In one or more embodiments of the invention, the nutritional product composition for the mind may include preparation of a synergistic blend of nutrients and a nutrient delivery system. In at least one embodiment the nutrient delivery system includes a liquid silicon dioxide, such as silica gel, that may be added to the synergistic blend. In one or more embodiments, the synergistic blend of nutrients is linked to the formation of acetylcholine, wherein acetylcholine may improve memory, focus and learning. In at least one embodiment, the liquid silicon dioxide, such as silica gel, may be added to the synergistic blend to increase the rate of metabolism of cells to increase the rate of absorption of the nutrients such that the levels of acetylcholine may be increased rapidly. In one or more embodiments, the liquid silicon dioxide or silica gel may include any or all of the following ingredients and may include a liquid such as water:

| Analyte | Amount |
| --- | --- |
| Aluminum | 25.7 ppm (w/w) |
| Antimony | 0.04 ppm (w/w) |
| Arsenic | <0.01 ppm (w/w) |
| Barium | 0.77 ppm (w/w) |
| Beryllium | 0.02 ppm (w/w) |
| Bismuth | <0.02 ppm (w/w) |
| Boron | 1.1 ppm (w/w) |
| Cadmium | 0.016 ppm (w/w) |
| Calcium | 140 ppm (w/w) |
| Chromium | 0.46 ppm (w/w) |
| Cobalt | 0.32 ppm (w/w) |
| Copper | 0.08 ppm (w/w) |
| Iron | 165 ppm (w/w) |
| Lead | <0.01 ppm (w/w) |
| Lithium | 0.1 ppm (w/w) |
| Magnesium | 53.0 ppm (w/w) |
| Manganese | 5.92 ppm (w/w) |
| Mercury | <0.005 ppm (w/w) |
| Molybdenum | 0.06 ppm (w/w) |
| Nickel | 0.30 ppm (w/w) |
| Phosphorous | <1 ppm (w/w) |
| Potassium | 74.9 ppm (w/w) |
| Selenium | 0.4 ppm (w/w) |
| Silver | <0.02 ppm (w/w) |
| Sodium | 53100 ppm (w/w) |
| Strontium | 2.72 ppm (w/w) |
| Thallium | <0.01 ppm (w/w) |
| Thorium | 0.01 ppm (w/w) |
| Tin | <0.01 ppm (w/w) |
| Titanium | 17.2 ppm (w/w) |
| Uranium | <0.01 ppm (w/w) |
| Vanadium | 0.90 ppm (w/w) |
| Zinc | 0.32 ppm (w/w) |
| Zirconium | 1.4 ppm (w/w) |
| Silicon Dioxide | |
| Silica | 6.58% (w/w) |

In a second embodiment of the invention, the nutritional product composition for the heart may include preparation of a synergistic blend of nutrients and a nutrient delivery system. In at least one embodiment the nutrient delivery system includes a liquid silicon dioxide, such as silica gel, that may be added to the synergistic blend. In one or more embodiments, the synergistic blend of nutrients is linked to increasing magnesium levels, specifically serum magnesium levels, wherein magnesium is a necessary electrolyte for muscle contractions as well as metabolic processes. In at least one embodiment, the liquid silicon dioxide, such as silica gel, may be added to the synergistic blend to increase the rate of metabolism of cells to increase the rate of absorption of the nutrients, such that the levels of magnesium may be increased rapidly.

In a third embodiment of the invention, the nutritional product composition for increasing energy using intracellular ATP production may include preparation of a synergistic blend of nutrients and a nutrient delivery system. In at least one embodiment the nutrient delivery system includes a liquid silicon dioxide, such as silica gel, that may be added to the synergistic blend. In one or more embodiments, the nutritional product composition for energy may increase intracellular ATP production through elevated fatty acid metabolism (beta oxidation). In at least one embodiment of the invention, the silica gel may be added to the synergistic blend of nutrients, such that the composition may increase the rate of metabolism of cells to increase the rate of absorption of the nutrients and increase energy production by the body rapidly.

In a fourth embodiment of the invention, the nutritional product composition for increasing human growth hormone and nitric oxide production may include a synergistic blend of nutrients and a nutrient delivery system. In at least one embodiment, the nutrient delivery system includes a liquid silicon dioxide, such as silica gel, that may be added to the synergistic blend. In at least one embodiment, the liquid silicon dioxide, such as silica gel, may be added to the synergistic blend to increase the rate of metabolism of cells and therefrom to increase the rate of absorption of the nutrients, such that the levels of producing the human growth hormone and elevating the nitric oxide levels may be increased rapidly.

Any of the embodiments described herein may be combined in full or part in order to create other blends that combine the effects of the various embodiments.

DETAILED DESCRIPTION OF THE INVENTION

Nutritional product compositions for the mind, the heart, energy levels using intracellular adenosine triphosphate (ATP) production, the human growth hormone, and nitric oxide production will now be described. Furthermore, methods of producing the nutritional product compositions will now be described. In the following exemplary description numerous specific details are set forth in order to provide a more thorough understanding of embodiments of the invention. It will be apparent, however, to an artisan of ordinary skill that the present invention may be practiced without incorporating all aspects of the specific details described herein. In other instances, specific features, quantities, or measurements well known to those of ordinary skill in the art have not been described in detail so as not to obscure the invention. Readers should note that although examples of the invention are set forth herein, the claims, and the full scope of any equivalents, are what define the metes and bounds of the invention.

In a first embodiment of the invention, the nutritional product composition for the mind, for example, may one or more of support mental performance and alertness, promote superior cognitive function, support focus, attention and memory, help with age-related declines in learning, organization and concentration, and help protect a user's brain from free radical damage. In at least on embodiment of the invention, the nutritional product composition for the mind provides an effective drug-delivery product for effective drug and nutrient administration.

In one or more embodiments, the nutritional product composition for the mind may include a synergistic blend of nutrients and a nutrient delivery system. In at least one embodiment, the nutrient delivery system includes a liquid silicon dioxide, such as silica gel, that may be added to the synergistic blend. In one or more embodiments, the synergistic blend of nutrients is linked to the formation of acetylcholine, wherein acetylcholine may improve memory, focus and learning. In at least one embodiment, the liquid silicon dioxide, such as silica gel, may be added to the synergistic blend to increase the rate of metabolism of cells and to increase the rate of absorption of the nutrients such that the levels of acetylcholine may be increased rapidly.

In at least one embodiment of the invention, the synergistic blend of nutrients includes or consists essentially of between 6 mg and 50 mg of phosphatidylserine, between 130 mg and 750 mg of dimethylaminoethanol (DMAE) bitartrate, between 30 mg and 1 g of citicholine, between 30 mg and 200 mg of alpha glycerylphosphorylcholine (GPC), and between 1000 and 7000 mg of fiber. In one or more embodiments, the silica gel may be between 2% and 10% of silicon dioxide by weight. In one or more embodiments, the synergistic blend may be dosed with the silica gel, wherein the dosing may vary depending on the nutrients and composition of the synergistic blend. In at least one embodiment of the invention, the silica gel is configured to increase an absorption rate of the synergistic blend.

In at least one embodiment of the invention, the nutritional product composition for the mind may be between 4000 mg and 7000 mg, such as 5800 mg. By way of one or more embodiments of the invention, the phosphatidylserine is between 20 mg and 50 mg, for example 27 mg of phosphatidylserine, the dimethylaminoethanol (DMAE) bitartrate is between 200 mg and 750 mg, for example 268 mg of dimethylaminoethanol (DMAE) bitartrate, the citicholine is between 75 mg and 1 g, for example 100.5 mg of citicholine, the alpha glycerylphosphorylcholine (GPC) is between 75 mg and 120 mg, for example 100.5 mg of alpha glycerylphosphorylcholine (GPC), and the fiber is between 3500 mg and 4500 mg, for example 4020 mg of fiber. In one or more embodiments, the silica gel may be between 5% and 8% by weight, for example 6.58%. In one or more embodiments, the synergistic blend is provided in a dry powder form that may be placed in water to easily be consumed by a user.

For example, the nutritional product composition for the mind synergistic blend may include the following nutrients:

| Component | Amount Per Serving | % Daily Value |
|---|---|---|
| Phosphatidylserine | 27 mg | * |
| DMAE Bitartrate | 268 mg | * |
| Citicholine | 100.5 mg | * |
| Alpha GPC | 100.5 mg | * |
| Fiber | 4020 mg | * |
| Dextrin | 2.5 g | * |
| D-Ribose | 500 mg | * |
| Lithothaminion Calcareum | 500 mg | * |

* Daily Value not established.
Other Ingredients: Erythritol, citric acid, natural flavors, natural color (from beet root juice), dicalcium phosphate dehydrate, stevia leaf extract, and silica.

In at least one embodiment of the invention, the phosphatidylserine may be obtained from a sunflower seed extract, the citicholine may include cognizin and the fiber may include nutriose. Furthermore, in at least one embodiment, the citicholine, such as, cognizin may elevate acetylcholine, improve focus and improve mental energy. The fiber, such as nutriose, for example, may aid in absorption of one or more nutrients. In at least one embodiment, DMAE may protect the user's brain from free radical damage, alpha GOC may enhance memory and cognition and help with age-related declines in learning, organization and concentration, and phosphatidylserine may support focus, attention and memory.

By way of at least one embodiment of the invention, the synergistic blend of nutrients may also include one or more of erythritol, dicalcium phosphate dehydrate, citric acid, and stevia. Furthermore, embodiments of the invention may include adding natural flavoring and natural sweetener, such as stevia, as needed and desired. In one or more embodiments, the natural color may be obtained from beet root juice.

In one or more embodiments of the invention, the nutritional product composition for the mind may elevate biochemical acetylcholine to improve memory, focus and learning, for example without the use of stimulants. The nutritional product composition for the mind may rapidly elevate acetylcholine levels in a user without requiring mega-dosing and/or without requiring a synthetic drug. For example, the nutritional product composition for the mind may increase acetylcholine levels, and improve mental clarity and focus in less than 10 minutes, once consumed.

In at least one embodiment of the invention, one or more of the nutritional product composition for the mind, the heart, energy using intracellular adenosine triphosphate (ATP) production, and human growth hormone and nitric oxide production may be provided in a single-serve packet, do not include artificial sweeteners, colors, preservatives or genetically modified organisms (GMO's) and may be gluten free.

In a second embodiment of the invention, the nutritional product composition for the heart, for example, may one or more of promote optimal heart function, support normal heart muscle contractions, contribute to the protection of cells against oxidative stress, support macronutrient metabolism and create a synergistic blend of sustenance for the heart on a cellular level. In addition, in embodiments of the invention, the nutritional product composition for the heart may reduce blood pressure without the need for a synthetic drug and may elevate serum magnesium levels. In at least one embodiment of the invention, the nutritional product composition for the heart may rapidly normalize blood pressure and increase magnesium levels in about 30 minutes, such as from 20 minutes to 40 minutes, or at least 30 minutes.

In at least on embodiment of the invention, the nutritional product composition for the heart provides an effective drug-delivery product for effective drug and nutrient administration.

In one or more embodiments, the nutritional product composition for the heart may include a synergistic blend of nutrients and a nutrient delivery system. In at least one embodiment, the nutrient delivery system includes a liquid silicon dioxide, such as silica gel, that may be added to the synergistic blend. In one or more embodiments, the synergistic blend of nutrients is linked to increasing magnesium levels, specifically serum magnesium levels, wherein magnesium is a necessary electrolyte for muscle contractions as well as metabolic processes. In at least one embodiment, the liquid silicon dioxide, such as silica gel, may be added to the synergistic blend to increase the rate of metabolism of cells and to increase the rate of absorption of the nutrients, such that the levels of magnesium may be increased rapidly.

In at least one embodiment of the invention, the synergistic blend of nutrients comprises between 15 mg and 100 mg of thiamin, between 5 mg and 50 mg of riboflavin, between 20 mg and 100 mg of niacin, between 5 mg and 50 mg of vitamin B6, between 100 mcg and 700 mcg of folate, between 5 mcg and 50 mcg of vitamin B12, between 15 mcg and 75 mcg of biotin, between 10 mg and 80 mg of pantothenic acid, between 15 mg and 100 mg of calcium, between 50 mg and 500 mg of magnesium, and between 1 mg and 10 mg of zinc. In one or more embodiments, the silica gel may be between 2% and 10% of silicon dioxide by weight. In one or more embodiments, the synergistic blend may be dosed with the silica gel, wherein the dosing may vary depending on the nutrients and composition of the synergistic blend. In at least one embodiment of the invention, the silica gel is configured to increase an absorption rate of the synergistic blend. In one or more embodiments, the synergistic blend may further include between 1 g and 7 g of dextrin (for example obtained from identity preserved maize, such as nutriose), between 200 mg and 800 mg of d-ribose and between 200 mg and 800 mg of lithothamnion calcareum (for example obtained from seaweed).

By way of one or more embodiments of the invention, the thiamin is between 40 mg and 60 mg, for example 50 mg of thiamin, the riboflavin is between 15 mg and 25 mg, for example 20 mg of riboflavin, the niacin is between 50 mg and 70 mg, for example 60 mg of niacin, the vitamin B6 is between 15 mg and 25 mg, for example 20 mg of vitamin B6, the folate is between 300 mcg and 500 mcg, for example 400 mcg of folate, the vitamin B12 is between 15 mcg and 30 mcg, for example 22 mcg of vitamin B12. In addition, in at least one embodiment, the biotin is between 35 mcg and 55 mcg, for example 45 mcg of biotin, the pantothenic acid is between 40 mg and 60 mg, for example 50 mg of pantothenic acid, the calcium is between 45 mg and 75 mg, for example 60 mg of calcium, the magnesium is between 150 mg and 300 mg, for example 250 mg of magnesium, and the zinc is between 3 mg and 7 mg, for example 5 mg of zinc. In one or more embodiments, the silica gel may be between 5% and 8% by weight, for example 6.58%. In one or more embodiments, the synergistic blend is provided in a dry powder form that may be placed in water to easily be consumed by a user.

For example, the nutritional product composition for the heart synergistic blend may include the following nutrients:

| Component | Amount Per Serving | % Daily Value |
| --- | --- | --- |
| Thiamin | 50 mg | 3333% |
| Riboflavin | 20 mg | 1176% |
| Niacin | 60 mg | 300% |
| Vitamin B6 | 20 mg | 1000% |
| Folate | 400 mcg | 100% |
| Vitamin B12 | 22 mcg | 367% |
| Biotin | 45 mcg | 15% |
| Pantothenic Acid | 50 mg | 500% |
| Calcium | 60 mg | 6% |
| Magnesium | 250 mg | 63% |
| Zinc | 5 mg | 33% |
| Dextrin | 2.5 g | * |
| D-Ribose | 500 mg | * |
| Lithothaminion Calcareum | 500 mg | * |

* Daily Value not established.
Other Ingredients: Erythritol, citric acid, natural flavors, beta-carotene (for color), malic acid, rebaudioside A (stevia lead extract), and silica.

In one or more embodiments of the invention, the thiamin may be thiamin hydrochloride, the riboflavin may be riboflavin-5-phosphate, the niacin may be niacinamide and nicotinic acid, the vitamin B6 may be pyridoxal-5-phosphate, the vitamin B12 may be methylcobalamin and the pantothenic acid may be calcium-d-pantothenate. Furthermore, in at least one embodiment, the calcium may be obtained from lithothamnion calcareum, such as from seaweed, the magnesium may be obtained from magnesium citrate and/or magnesium bisglycinate, and the zinc may be zinc gluconate.

In one or more embodiments, the nutritional product composition for the heart may further include ingredients from one or more of erythritol, natural flavor, natural color, citric acid, malic acid, rebaudioside A (such as *stevia* lead extract). The natural color, for example, may be provided from beta-carotene.

In a third embodiment of the invention, the nutritional product composition for energy using intracellular ATP production, for example, may naturally assist the body in making more energy, without the use of caffeine and/or stimulants. In at least one embodiment, the nutritional product composition for energy may include trimethylglycine (TMG), which may increase intracellular oxygen levels, alpha-ketoglutaric acid (AKG), which may be an intermediary in the krebs cycle, L-carnitine, which may increase fatty acid metabolism, B-Complex vitamins and antioxidant activity for supporting body energy. In at least one embodiment of the invention, the nutritional product composition for energy may combat fatigue on a cellular level and may be a crash-free and stimulant free formula, and may increase a user's energy level, and experience a physiological response, in less than 10 minutes, once consumed.

In at least on embodiment of the invention, the nutritional product composition for energy provides an effective drug-delivery product for effective drug and nutrient administration.

In one or more embodiments, the nutritional product composition for energy may include a synergistic blend of nutrients and a nutrient delivery system. In at least one embodiment, the nutrient delivery system includes a liquid silicon dioxide, such as silica gel, that may be added to the synergistic blend. In one or more embodiments, the nutritional product composition for energy may increase intracellular ATP production through elevated fatty acid metabolism (beta oxidation). In at least one embodiment of the invention, the silica gel may be added to the synergistic blend of nutrients, such that the composition may increase the rate of metabolism of cells to increase the rate of absorption of the nutrients and increase energy production by the body rapidly. For example, in one or more embodiments, the L-carnitine may increase the availability of fat for conversion into energy, and the trimethylglycine (TMG) may provide the oxygen necessary for such a conversion.

In at least one embodiment of the invention, the synergistic blend of nutrients comprises between 50 mg and 500 mg of vitamin C, between 0.5 mg and 5 mg of thiamine, between 0.5 mg and 5 mg of riboflavin, between 10 mg and 50 mg of niacin, between 0.5 mg and 5 mg of vitamin B6, between 100 mcg and 700 mcg of folate, between 5 mcg and 50 mcg of vitamin B12, between 15 mcg and 85 mcg of d-biotin, between 1 mg and 20 mg of pantothenic acid, between 5 mg and 50 mg of calcium, between 10 mcg and 100 mcg of selenium, between 0.1 mg and 1 mg of copper, and between 10 mcg and 100 mcg of chromium In one or more embodiments, the silica gel may be between 2% and 10% of silicon dioxide by weight. In one or more embodiments, the synergistic blend may be dosed with the silica gel, wherein the dosing may vary depending on the nutrients and composition of the synergistic blend. In at least one embodiment of the invention, the silica gel is configured to increase an absorption rate of the synergistic blend. In one or more embodiments, the synergistic blend may further include between 100 mg and 1 g of L-carnitine, between 200 mg and 800 mg of alpha-ketoglutaric acid (AKG), between 100 mg and 800 mg of trimethylglycine (TMG) and between 10 mg and 100 mg of grape seed extract.

By way of one or more embodiments of the invention, the vitamin C is between 100 mg and 300 mg, for example 200 mg of vitamin C, the thiamine is between 1 mg and 2 mg, for example 1.5 mg of thiamine, the riboflavin is between 1 mg and 2 mg, for example 1.7 mg of riboflavin, the niacin is between 20 mg and 40 mg, for example 30 mg of niacin, the vitamin B6 is between 1 mg and 3 mg, for example 2 mg of vitamin B6, the folate is between 300 mcg and 500 mcg, for example 400 mcg of folate, the vitamin B12 is between 15 mcg and 30 mcg, for example 22 mcg of vitamin B12. In addition, in at least one embodiment, the d-biotin is between 40 mcg and 60 mcg, for example 50 mcg of d-biotin, the pantothenic acid is between 5 mg and 15 mg, for example 10 mg of pantothenic acid, the calcium is between 15 mg and 30 mg, for example 22 mg of calcium, the selenium is between 30 mcg and 70 mcg, for example 50 mcg of selenium, the copper is between 0.2 mg and 0.7 mg, for example 0.5 mg of copper, and the chromium is between 35 mcg and 65 mcg, for example 50 mcg of chromium. In one or more embodiments, the silica gel may be between 5% and 8% by weight, for example 6.58%. In one or more embodiments, the synergistic blend is provided in a dry powder form that may be placed in water to easily be consumed by a user.

For example, the nutritional product composition for energy synergistic blend may include the following nutrients:

| Component | Amount Per Serving | % Daily Value |
|---|---|---|
| Vitamin C | 200 mg | 333% |
| Thiamin | 1.5 mg | 100% |
| Riboflavin | 1.7 mg | 100% |
| Niacin | 30 mg | 150% |
| Vitamin B6 | 2 mg | 100% |
| Folate | 400 mcg | 100% |
| Vitamin B12 | 22 mcg | 367% |
| D-Biotin | 50 mcg | 17% |
| Pantothenic Acid | 10 mg | 100% |
| Calcium | 22 mg | 2% |
| Selenium | 50 mcg | 71% |
| Copper | 0.5 mg | 25% |
| Chromium | 50 mcg | 42% |
| L-Carnitine | 500 mg | * |
| AKG | 500 mg | * |
| TMG | 400 mg | * |
| Grape seed extract | 50 mg | * |

* Daily Value not established.
Other Ingredients: Erythritol, Identity Preserved Corn Dextrin, natural flavors, natural red color (beet juice powder, annatto extract), rebaudioside A (stevia lead extract), malic acid and silica.

In one or more embodiments of the invention, the vitamin C may be calcium ascorbate and calcium threonate, the thiamin may be thiamin hydrochloride, the riboflavin may be riboflavin-5-phosphate, the niacin may be inositol hexanicotinate and niacin, the vitamin B6 may be pyridoxal-5-phosphate, the vitamin B12 may be methylcobalamin and the pantothenic acid may be calcium-d-pantothenate. Furthermore, in at least one embodiment, the calcium may be calcium ascorbate and calcium threonate, the selenium may be selenomethionine, the copper may be copper gluconate, the chromium may be chromium picolinate, and the grape seed extract may be 95% oligomeric proanthocyanidins.

In one or more embodiments, the synergistic blend may further include between 100 mg and 1 g of L-carnitine, between 200 mg and 800 mg of alpha-ketoglutaric acid (AKG), between 100 mg and 800 mg of trimethylglycine (TMG) and between 10 mg and 100 mg of grape seed extract.

In at least one embodiment, the nutritional product composition for energy may further include ingredients from one or more of erythritol, natural flavor, natural color, malic acid, rebaudioside A, and identity preserved corn dextrin, and wherein said natural color is provided from beet juice powder and annatto extract. In one or more embodiments, the flavoring and sweetener may be added, removed and modified to the nutritional composition as desired.

In a fourth embodiment of the invention, the nutritional product composition for increasing human growth hormone and nitric oxide production, for example, may one or more of elevate the production of the human growth hormone and elevate the nitric oxide levels. The human growth hormone, for example, may increase lean muscle mass and decrease body fat. Nitric oxide, for example, may be a vasodilator associated with cardiovascular health, hair growth, male sexual performance and immune function. In at least on embodiment of the invention, the nutritional product composition for increasing human growth hormone and nitric oxide production provides an effective drug-delivery product for effective drug and nutrient administration.

In one or more embodiments, the nutritional product composition for increasing human growth hormone and nitric oxide production may include a synergistic blend of nutrients and a nutrient delivery system. In at least one embodiment, the nutrient delivery system includes a liquid silicon dioxide, such as silica gel, that may be added to the synergistic blend. In at least one embodiment, the liquid silicon dioxide, such as silica gel, may be added to the synergistic blend to increase the rate of metabolism of cells to increase the rate of absorption of the nutrients such that the levels of producing the human growth hormone and elevating the nitric oxide levels may be increased rapidly.

In at least one embodiment of the invention, the synergistic blend of nutrients comprises between 0.5 g and 3 g of colostrum, between 0.75 g and 6.5 g of L-arginine, between 100 mg and 750 mg of potassium citrate, and between 30 mg and 400 mg of goji berry extract. Embodiments of the L-arginine may be utilized in multiple forms including L-arginine aspartate and L-arginine HCL for example. In one embodiment, the 0.75 g to 6.5 g amount of L-arginine may include between 0.25 g and 1.5 g of L-arginine aspartate and between 0.5 g to 5 g L-arginine HCL. In one or more embodiments, the silica gel may be between 2% and 10% of silicon dioxide by weight. In one or more embodiments, the synergistic blend may be dosed with the silica gel, wherein the dosing may vary depending on the nutrients and composition of the synergistic blend. In at least one embodiment of the invention, the silica gel is configured to increase an absorption rate of the synergistic blend.

By way of one or more embodiments of the invention, the colostrum is between 0.75 g and 2 g, for example 1.5 g of colostrum, the L-arginine is between 2 g and 4 g, for example 3 g of L-arginine, the potassium citrate is between 400 mg and 600 mg, for example 500 mg of potassium citrate, and the goji berry extract is between 50 mg and 200 mg, for example 100 mg of goji berry extract. The 2 g to 4 g of L-arginine may include between 0.5 g and 1 g of L-arginine aspartate and between 1.5 g to 3 g L-arginine HCL in this embodiment. Another embodiment that utilizes 3.5 g of L-arginine, may include 0.5 g of L-arginine aspartate and between 3 g of L-arginine HCL for example. In one or more embodiments, the silica gel may be between 5% and 8% by weight, for example 6.58%. In one or more embodiments, the synergistic blend is provided in a dry powder form that may be placed in water to easily be consumed by a user. Furthermore, embodiments of the invention may include adding, removing and/or modifying natural flavoring and natural sweetener, to and from the nutritional product composition, as needed and desired.

In one or more embodiments of the invention, the nutritional product composition for increasing human growth hormone and nitric oxide production may show improvements in feelings of wellness and production of human growth hormones and nitric oxide in about 30 minutes, such as from 20 minutes to 40 minutes, or at least 30 minutes. For example, the nutritional product composition for the mind synergistic blend may include the following nutrients:

| Component | Amount Per Serving | % Daily Value |
|---|---|---|
| Colostrum | 27 mg | * |
| L-Arginine | 268 mg | * |
| Potassium Citrate | 100.5 mg | * |
| Goji Berry Extract | 100.5 mg | * |

* Daily Value not established.
Other Ingredients: Erythritol, citric acid, natural flavors, natural color, stevia leaf extract, and silica.

In at least one embodiment of the invention, a synergistic blend of nutrients may include one or more of the nutrients disclosed in one or more of the nutritional product compositions for the mind, the nutritional product composition the heart, the nutritional product composition for energy levels using intracellular adenosine triphosphate (ATP) production, and the nutritional product composition the human growth hormone and nitric oxide production.

According to one or more embodiments of the invention, the silica in one or more of the nutritional product compositions for the mind, the heart, energy levels using intracellular adenosine triphosphate (ATP) production, and human growth hormone and nitric oxide production may include a proprietary modified sodium silicate. In at least one embodiment, a chemical structure of the proprietary modified sodium silicate may be determined using nuclear magnetic resonance (NMR) and infrared (IR) spectroscopy. In one or more embodiments, the silica may include a mixture of trimeric sodium silicate and sodium silicate pentahydrate.

In at least one embodiment of the invention, the silica ($SiO_2$) in one or more of the nutritional product compositions for the mind, the heart, energy levels using intracellular adenosine triphosphate (ATP) production, and human growth hormone and nitric oxide production may be a silicic acid anhydride of monomeric ortho-silicic acid ($H_4SiO_4$) that may include one or more biological and therapeutic effects wherein the silica may be water-soluble and may be stable in highly diluted aqueous solutions. According to one or more embodiments, an end product of the silica may be hydrated silica ($SiO_2.xH_2O$) such as colloidal silicic acid or hydrated silica gel. In embodiments of the invention, the silica may be accompanied by dehydration yielding less hydrated silicon dioxide ($SiO_2$) phases, such as a silica gel or amorphous silicon dioxide. In one or more embodiments of the invention, the ortho-silicic acid may stimulate collagen production and may be used for connective tissue function and repair.

While the invention herein disclosed has been described by means of specific embodiments and applications thereof, numerous modifications and variations could be made thereto by those skilled in the art without departing from the scope of the invention set forth in the claims.

What is claimed is:

1. A nutritional product composition for increasing human growth hormone and nitric oxide production comprising:
   a synergistic blend of nutrients; and
   a silica gel;
   wherein said synergistic blend of nutrients comprises
      between 0.5 g and 5 g of colostrum;
      between 0.75 g and 6.5 g of L-arginine comprising
         between 0.25 g and 1.5 g of L-arginine aspartate and
         between 0.5 g to 5 g L-arginine HCL;
      between 100 mg and 750 mg of potassium citrate; and
      between 30 mg and 1 g of goji berry extract;
   wherein said silica gel is between 2% and 10% by weight and is configured to increase an absorption rate of said synergistic blend.

2. The nutritional product composition of claim 1, wherein said colostrum is between 0.75 g and 2 g.

3. The nutritional product composition of claim 1, wherein said L-arginine is between 2 g and 4 g and comprises
   between 0.5 g and 1 g of L-arginine aspartate and
   between 1.5 g to 3 g L-arginine HCL.

4. The nutritional product composition of claim 1, wherein said L-arginine comprises approximately 3.5 g and comprises
   approximately 0.5 g of L-arginine aspartate and
   approximately 3 g L-arginine HCL.

5. The nutritional product composition of claim 1, wherein said potassium citrate is between 400 mg and 600 mg.

6. The nutritional product composition of claim 1, wherein said goji berry extract is between 50 mg and 200 mg.

7. The nutritional product composition of claim 1, wherein said silica gel is between 5% and 8% by weight.

8. The nutritional product composition of claim 1, wherein said synergistic blend of nutrients is configured to increase human growth hormone levels and nitric oxide levels.

9. The nutritional product composition of claim 1, wherein said silica gel is further configured to increase the rate of metabolism of the synergistic blend and increase human growth hormone production and nitric oxide production.

10. A method for producing a nutritional product composition for increasing human growth hormone and nitric oxide production comprising:
   preparing a synergistic blend of nutrients, wherein said nutrients comprise
      between 0.5 g and 5 g of colostrum;
      between 0.75 g and 6.5 g of L-arginine comprising
         between 0.25 g and 1.5 g of L-arginine aspartate and
         between 0.5 g to 5 g L-arginine HCL;
      between 100 mg and 750 mg of potassium citrate; and
      between 30 mg and 1 g of goji berry extract;
   adding a silica gel to said synergistic blend;
      wherein said silica gel is configured to increase an absorption rate of said synergistic blend, and
      wherein said silica gel comprises between 2% and 10% of silicon dioxide by weight.

* * * * *